United States Patent
Bando et al.

(10) Patent No.: US 12,140,600 B2
(45) Date of Patent: Nov. 12, 2024

(54) METHOD FOR MEASURING ACTIVATED PARTIAL THROMBOPLASTIN TIME

(71) Applicant: SYSMEX CORPORATION, Kobe (JP)

(72) Inventors: Takahiko Bando, Kobe (JP); Kohei Akatsuchi, Kobe (JP); Naoki Yamamoto, Kobe (JP); Masako Aki, Kobe (JP); Hiroshi Negoro, Kobe (JP); Masato Michishita, Kobe (JP)

(73) Assignee: SYSMEX CORPORATION, Kobe (JP)

( * ) Notice: Subject to any disclaimer, the term of this patent is extended or adjusted under 35 U.S.C. 154(b) by 471 days.

(21) Appl. No.: 17/029,933

(22) Filed: Sep. 23, 2020

(65) Prior Publication Data

US 2021/0088537 A1   Mar. 25, 2021

(30) Foreign Application Priority Data

Sep. 24, 2019 (JP) ................. 2019-173297

(51) Int. Cl.
*G01N 33/86* (2006.01)

(52) U.S. Cl.
CPC .................... *G01N 33/86* (2013.01)

(58) Field of Classification Search
CPC .......... G01N 33/86; G01N 33/49; C12Q 1/56
See application file for complete search history.

(56) References Cited

U.S. PATENT DOCUMENTS

| | | | |
|---|---|---|---|
| 5,055,412 A | 10/1991 | Proksch | |
| 2017/0059594 A1* | 3/2017 | Yoshida | ............. G01N 33/86 |

FOREIGN PATENT DOCUMENTS

| | | |
|---|---|---|
| CN | 108226539 A | 6/2018 |
| CN | 109613279 A | 4/2019 |
| DE | 2915310 A1 | 10/1980 |
| DE | 102008008537 A1 | 8/2009 |
| EP | 3136105 A1 | 3/2017 |
| IL | 59816 A | 10/1983 |
| JP | S55-149298 A | 11/1980 |
| JP | H07-151763 A | 6/1995 |
| JP | 2013-205087 A | 10/2013 |
| JP | 2017-049040 A | 3/2017 |
| WO | 89/011643 A1 | 11/1989 |
| WO | 2015/194165 A1 | 12/2015 |

OTHER PUBLICATIONS

Lin, Zhucan et al. "Chemical Constituents from Sedum Aizoon and Their Hemostatic Activity." Pharmaceutical biology 52.11 (2014):1429-1434. (Year: 2014).*
Appendix A—"Activated partial thromboplastin time (APTT) test | Definitions+Normal Ranges", Ben, Aug. 15, 2018, retrieved from https://blog.healthmatters.io/2018/08/15/activated-partial-thromboplastin-time-aptt-test-definitionsnormal-ranges/ on Sep. 13, 2023. (Year: 2018).*
The extended European Search Report issued on Mar. 3, 2021 in a counterpart European patent application No. 20197998.6.
The Japanese Office Action issued on Aug. 29, 2023 in a counterpart Japanese patent application No. 2019-173297.
The Communication pursuant to Article 94(3) EPC issued on Jun. 28, 2023 in a counterpart European patent application No. 20197998.6.
Chinese Office Action issued on Jun. 24, 2024 in a counterpart Chinese patent application No. 202010996041.6.

* cited by examiner

*Primary Examiner* — Louise W Humphrey
*Assistant Examiner* — John Paul Selwanes
(74) *Attorney, Agent, or Firm* — Sughrue Mion, PLLC (57) ABSTRACT

Disclosed is a method for measuring activated partial thromboplastin time, the method comprising: mixing: a blood sample; a first reagent comprising an ellagic acid compound and a compound represented by Formula (I); and a second regent comprising a calcium ion; and measuring activated partial thromboplastin time using the mixture prepared in the mixing step, wherein the compound represented by Formula (I) is shown below

[Chem. 1]

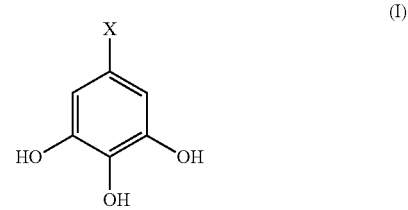

(I)

wherein X is a hydrogen atom, —(C=O)—Y, or —(C=O)—OZ, Y is a hydroxyl group, a hydrogen atom, a linear or branched alkyl group having a carbon number of 1 or more and 6 or less, or a phenyl group, and Z is an alkali metal.

13 Claims, 5 Drawing Sheets

METHOD FOR MEASURING ACTIVATED PARTIAL THROMBOPLASTIN TIME

CROSS REFERENCE TO RELATED APPLICATIONS

This application claims priority from prior Japanese Patent Application No. 2019-173297, filed on Sep. 24, 2019, entitled "Reagent and reagent kit for activated partial thromboplastin time measurement and method for suppressing precipitation of ellagic acid compound", the entire contents of which are incorporated herein by reference.

FIELD OF THE INVENTION

The present invention relates to a method for measuring activated partial thromboplastin time.

BACKGROUND

Since ellagic acid activates the contact factor system, ellagic acid is often used in reagents for activated partial thromboplastin time (APTT) measurement as a coagulation activator. However, ellagic acid is likely to precipitate in aqueous solvents which may be used in APTT measurement reagents. When ellagic acid precipitates, the ellagic acid required for the coagulation reaction is insufficient and the coagulation time cannot be accurately measured. Conventionally, phenol has been added to reagents for APTT measurement containing ellagic acid as a substance which suppresses the precipitation of ellagic acid. However, phenol is an environmentally hazardous substance, and regulations on the use of phenol have been stricter. Hence, reagents for APTT measurement are desired which do not substantially contain phenol and in which the precipitation of ellagic acid is suppressed. For example, Japanese Laid-Open Patent Publication No. 2013-205087 describes that amino acids having aromatic rings are added to reagents for APTT measurement as a substance which suppresses the precipitation of ellagic acid. U.S. Patent Application Publication No. 2017/0059594 describes that a polyvinyl alcohol compound is added to reagents for APTT measurement as a substance which suppresses the precipitation of ellagic acid.

SUMMARY OF THE INVENTION

The scope of the present invention is defined solely by the appended claims, and is not affected to any degree by the statements within this summary.

The present inventors have completed the present invention by finding out that a compound represented by Formula (I) suppresses the precipitation of an ellagic acid compound. Consequently, the present invention provides A method for measuring activated partial thromboplastin time, the method comprising: mixing: a blood sample; a first reagent comprising an ellagic acid compound and a compound represented by Formula (I); and a second regent comprising a calcium ion; and measuring activated partial thromboplastin time using the mixture prepared in the mixing step, wherein the compound represented by Formula (I) is shown below

[Chem. 1]

(I)

wherein
X is a hydrogen atom, —(C=O)—Y, or —(C=O)—OZ,
Y is a hydroxyl group, a hydrogen atom, a linear or branched alkyl group having a carbon number of 1 or more and 6 or less, or a phenyl group, and
Z is an alkali metal.

DETAILED DESCRIPTION OF THE PREFERRED EMBODIMENTS

[1. Reagent for Activated Partial Thromboplastin Time Measurement]

The APTT reagent of the present embodiment contains a compound represented by Formula (I) as a substance which suppresses the precipitation of ellagic acid.

[Chem. 2]

(I)

wherein
X is a hydrogen atom, —(C=O)—Y, or —(C=O)—OZ,
Y is a hydroxyl group, a hydrogen atom, a linear or branched alkyl group having a carbon number of 1 or more and 6 or less, or a phenyl group, and
Z is an alkali metal.

Examples of the linear or branched alkyl group having a carbon number of 1 or more and 6 or less in Formula (I) include groups such as methyl, ethyl, propyl, butyl, pentyl, hexyl, isopropyl, isobutyl, isopentyl (isoamyl), and isohexyl. When X in Formula (I) is —(C=O)—OZ, Formula (I) represents an alkali metal salt of gallic acid. Examples of the alkali metal include sodium, potassium, and lithium. Among these, sodium and potassium are preferable.

Examples of the compound represented by Formula (I) include pyrogallol, gallic acid, 3,4,5-trihydroxybenzaldehyde, methyl gallate, ethyl gallate, propyl gallate, butyl gallate, pentyl gallate, hexyl gallate, isopropyl gallate, isobutyl gallate, isopentyl gallate (isoamyl gallate), isohexyl gallate, benzopyrogallol (3,4,5-trihydroxybenzophenone), sodium gallate, and potassium gallate. Among these, pyrogallol and gallic acid are preferable.

The concentration of the compound represented by Formula (I) in the APT reagent can be determined depending on the concentration of the ellagic acid compound in the reagent. When the concentration of the ellagic acid compound in the APTT reagent is the extent to which the ellagic acid compound is usually used for APTT measurement, the concentration of the compound represented by Formula (I) in the APTT reagent is, for example, 0.001% by mass or more and 0.02% by mass or less, preferably 0.005% by mass or more and 0.02% by mass or less. In a preferred embodiment, the mass of the compound represented by Formula (I) in the APTT reagent is 5 parts by mass or more and 65 parts by mass or less, more preferably 20 parts by mass or more and 65 parts by mass or less per 100 parts by mass of the ellagic acid compound.

The APTT reagent of the present embodiment contains an ellagic acid compound as an activator. The ellagic acid compound may be any of ellagic acid, a salt of ellagic acid, or a metal complex of ellagic acid. The central metal of the metal complex may be an ion or an atom. The central metals may be the same as or different from each other in the metal complexes of ellagic acid. A metal ion complex of ellagic acid is particularly preferable as the ellagic acid compound from the viewpoint of strength of the activation action. Examples of the metal ion comprise zinc ion, aluminum ion, and manganese ion. The concentration of the ellagic acid compound in the APTT reagent is usually 10 μM or more and 400 μM or less, preferably 30 μM or more and 150 μM or less.

In the present embodiment, an activator other than the ellagic acid compound may be further comprised. Such an activator may be any substance which activates the contact factor in the intrinsic coagulation pathway, and examples thereof comprise silica, kaolin, and celite. When the activator is, for example, silica, the concentration of this activator in the APTT reagent is usually 0.1 mg/mL or more and 1.0 mg/mL or less, preferably 0.2 mg/mL or more and 0.6 mg/mL or less.

The APTT reagent of the present embodiment preferably comprises a phospholipid. Examples of the phospholipid include phosphatidylethanolamine (PE), phosphatidylcholine (PC), and phosphatidylserine (PS). The APTT reagent of the present embodiment comprises preferably at least one selected from the group consisting of PE, PC, and PS, more preferably PE, PC, and PS. The phospholipid may be a naturally-derived phospholipid or a synthetic phospholipid. Examples of the naturally-derived phospholipid comprise phospholipids derived from rabbit brain, bovine brain, human placenta, soybean, and egg yolk. In particular, a synthetic phospholipid or a naturally-derived phospholipid purified to a purity of 99% or more is preferable.

The fatty acid side chain (acyl group) of PE, PC, and PS is not particularly limited, and examples thereof comprise an acyl group having a carbon number of 8 or more and 20 or less, preferably a carbon number of 14 or more and 18 or less. Examples of such an acyl group comprise lauroyl group, myristoyl group, palmitoyl group, stearoyl group and oleoyl group. PE, PC, and PS all have two fatty acid side chains in the molecule. The two fatty acid side chains in each molecule of PE, PC, and PS may be the same as or different from each other.

Specific examples of PE comprise dilauroylphosphatidylethanolamine, dimyristoylphosphatidylethanolamine, dipalmitoylphosphatidylethanolamine, distearoylphosphatidylethanolamine, and dioleoylphosphatidylethanolamine. Specific examples of PC comprise dilauroylphosphatidylcholine, dimyristoylphosphatidylcholine, dipalmitoylphosphatidylcholine, distearoylphosphatidylcholine, and dioleoylphosphatidylcholine. Specific examples of PS comprise dilauroylphosphatidylserine, dimyristoylphosphatidylserine, dipalmitoylphosphatidylserine, distearoylphosphatidylserine, and dioleoylphosphatidylserine.

The concentration of the phospholipid in the APTT reagent can be appropriately determined depending on the kind of phospholipid, the measurement conditions, and the like. For example, the concentration of phospholipid in the APTT reagent is 30 to 2000 μg/mL, preferably 60 to 1000 μg/mL. When the APTT reagent contains PE, PC, and PS as the phospholipid, the PE concentration in the reagent is usually 10 to 700 μg/mL, preferably 30 to 300 μg/mL, the PC concentration in the reagent is usually 20 to 1000 μg/mL, preferably 30 to 500 μg/mL, and the PS concentration in the reagent is usually 3 to 300 μg/mL, preferably 5 to 150 μg/mL.

The APTT reagent of the present embodiment preferably comprises a metal ion. It is expected that a metal ion activates the contact factor and suppresses the generation of precipitates. Ellagic acid in the reagent forms a chelate with the metal ion to be a metal ion complex of ellagic acid. The APTT reagent comprising a metal ion can be prepared by adding a metal ion-forming compound to the APTT reagent. A metal ion-forming compound is a compound broken down into a metal ion and the others when it dissolves in an aqueous solution. The metal ion-forming compound is not particularly limited as long as it generates a metal ion in the APTT reagent and an anion generated from this compound does not inhibit the blood coagulation reaction. Examples of the metal ion-forming compound include salts of metals and organic acids or inorganic acids. Among these, salts of metals and inorganic acids are preferable, and examples thereof include salts of metals and acids such as hydrochloric acid, sulfuric acid, and nitric acid. More preferred metal salts comprise at least one selected from a zinc salt, a manganese salt, an aluminum salt, or a nickel salt. The metal ion-forming compound may be one kind or a combination of two or more kinds. In a preferred embodiment, the metal ion-forming compound comprises a zinc ion compound and an aluminum ion-forming compound or comprises a manganese ion-forming compound with an aluminum ion-forming compound. Examples of such compounds include zinc chloride, manganese chloride, aluminum chloride, and nickel chloride. The metal ion-forming compound may be an anhydride or a hydrate. The concentration of the metal ion in the APTT reagent is, for example, 1 μM or more and 1 mM or less, preferably 10 μM or more and 500 μM or less.

The APTT reagent of the present embodiment may further contain a nonpolar amino acid for stability improvement. Examples of the nonpolar amino acid include glycine, alanine, and phenylalanine. Glycine also functions as a buffer and phenylalanine also functions as a precipitation inhibitor of ellagic acid, and thus glycine and phenylalanine are preferable as the nonpolar amino acid. The nonpolar amino acid may be any of an L-form, a D-form, or a mixture thereof. The nonpolar amino acid may be a naturally-derived amino acid or a synthetic amino acid. The concentration of the nonpolar amino acid in the APTT reagent can be appropriately set but is usually 0.75% by mass or more, preferably 0.75% by mass or more and 5% by mass or less, more preferably 0.75% by mass or more and 1.5% by mass or less.

The APTT reagent of the present embodiment may further contain an additive for improving the storage stability and stability. Examples of such an additive include a preservative, an antioxidant, and a stabilizer. Examples of the preservative include an antibiotic such as an aminoglycoside antibiotic and sodium azide. A commercially available preservative such as ProClin (trademark) 300 may be added. Examples of the antioxidant include butylhydroxyanisole. Examples of the stabilizer include polyethylene glycol and polyvinylpyrrolidone.

The solvent used in the APTT reagent of the present embodiment can be appropriately selected from the aqueous solvents which are usually used in the field of blood test. Examples of such aqueous solvents include water, physiological saline, and a buffer solution. The pH of the buffer solution is preferably 6 or more and 8 or less, more preferably 7 or more and 7.6 or less. Examples of the buffer solution include Good buffer solutions such as HEPES, TAPS, MOPS, BES, and TES, Tris-HCl buffer solution (Tris-HCl), Orenberonal buffer solution, and imidazole-HCl buffer solution. The buffer contained in the buffer solution may be one kind or two or more kinds. Glycine may be added to the buffer solution if necessary.

The pH of the APTT reagent of the present embodiment is usually 6 or more and 8 or less, preferably 7 or more and 7.6 or less. The pH of the APTT reagent can be adjusted by adding the buffer solution described above.

As the APTT reagent of the present embodiment contains the compound represented by Formula (I), it is possible not only to prevent the precipitation of ellagic acid but also to decrease the abnormal initial reaction in the optical measurement of APTT. Abnormal initial reaction refers to a phenomenon in which the optical measurement value of the sample changes immediately after the APTT reagent is added to the blood sample. When a normal blood sample and APTT reagent are mixed together, usually the optical measurement value of the sample hardly changes during the period from the addition of the reagent to the deposition of fibrin (the start of coagulation), and the optical measurement value greatly changes from the time of fibrin deposition. However, an abnormal initial reaction may occur in a blood sample of a patient with abnormal coagulation. Depending on the measuring instrument, it may not be possible to acquire an accurate coagulation time when an abnormal initial reaction is detected.

The APTT reagent of the present embodiment can be produced in the same manner as the conventional method for producing an APTT reagent except that the compound represented by Formula (I) is used instead of phenol as a precipitation inhibitor of ellagic acid. As an example, the: preparation of the APTT reagent of the present embodiment containing a phospholipid will be described. First, ellagic acid or a salt of ellagic acid is dissolved in an aqueous solvent to prepare an aqueous solution of ellagic acid. Good buffer is preferable as the aqueous solvent. A metal ion-forming compound is added to the ellagic acid solution obtained to prepare a solution containing a metal ion complex of ellagic acid. The above-mentioned phospholipid is added to the solution obtained, whereby the APTT reagent of the present embodiment containing a phospholipid can be obtained. If necessary, the above-mentioned nonpolar amino acid, preservative, antioxidant, stabilizer and the like may be added to the APTT reagent The APTT reagent of the present embodiment can be used under general APTT measurement conditions as the conventional APTT reagent. The APTT reagent of the present embodiment can be used for a screening test for an endogenous coagulation factor, and monitoring of heparin therapy, and a screening test for lupus anticoagulant (LA) as the conventional APTT reagent. The mixing ratio of the APTT reagent of the present embodiment to the blood sample may be about 8:2 to 2:8 and is preferably 5:5 as a volume ratio. In other words, the amount of the APTT reagent of the present embodiment added may be an amount (volume) to be 0.25 time or more and 4 times or less the amount (volume) of the blood sample. Preferably, the amount of the APTT reagent of the present embodiment added is equal to the amount (volume) of the blood sample.

When the coagulation time of a normal sample is measured using the APTT reagent of the present embodiment, it is possible to attain a measurement result to the same extent as that by the conventional APTT reagent. For example, when the APTT reagent of the present embodiment is appropriately used together with a calcium ion-containing aqueous solution to measure the APTT of a predetermined normal plasma (for example, Coagtrol IX manufactured by Sysmex Corporation), APTT is desirably around 30 seconds (for example, 25 seconds or more and 35 seconds or less). When APTT of a predetermined abnormal plasma (for example, Coagtrol IIX manufactured by Sysmex Corporation) is measured, APTT is desirably within a range of 60 to 100 seconds.

Figure 1:
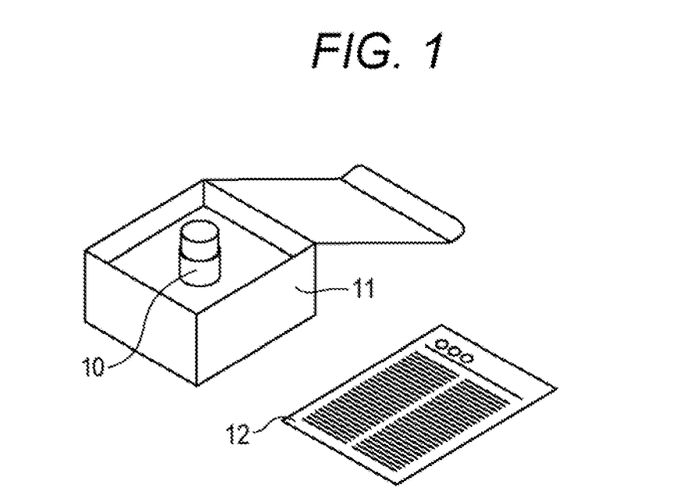
FIG. 1 is a schematic diagram illustrating an example of an APTT reagent of the present embodiment.

In the present embodiment, a case accommodating the APTT reagent may be packed in a box and provided to the user. The package insert describing how to use the APTT reagent and the like may be enclosed in the box. FIG. 1 illustrates an example of the APTT reagent of the present embodiment. With reference to FIG. 1, 10 indicates a case accommodating the APTT reagent of the present embodiment, 11 indicates a packing box, and 12 indicates a package insert.

[2. Reagent Kit for Activated Partial Thromboplastin Time Measurement]

The reagent kit for APTT measurement of the present embodiment (hereinafter, also referred to as "reagent kit") contains a first reagent containing an ellagic acid compound and a compound represented by Formula (I) and a second reagent containing a calcium salt. The APTT reagent of the present embodiment described above can be used as the first reagent. The details of the first reagent are the same as those described for the APTT reagent of the present embodiment. The details of the ellagic acid compound are as described above.

The second reagent is a reagent which is added to the mixture of a blood sample with the first reagent and starts blood coagulation. The second reagent is preferably a calcium ion-containing aqueous solution. As the calcium ion-containing aqueous solution, an aqueous solution of a calcium salt is preferable. Examples of the calcium salt include calcium chloride. The calcium ion concentration in the second reagent is usually 2.5 mM or more and 40 mM or less, preferably 10 mM or more and 30 mM or less. When a calcium salt such as calcium chloride that is easily dissolved in water is used, the calcium ion concentration in the second reagent may be expressed by the concentration of the calcium salt.

Figure 2:
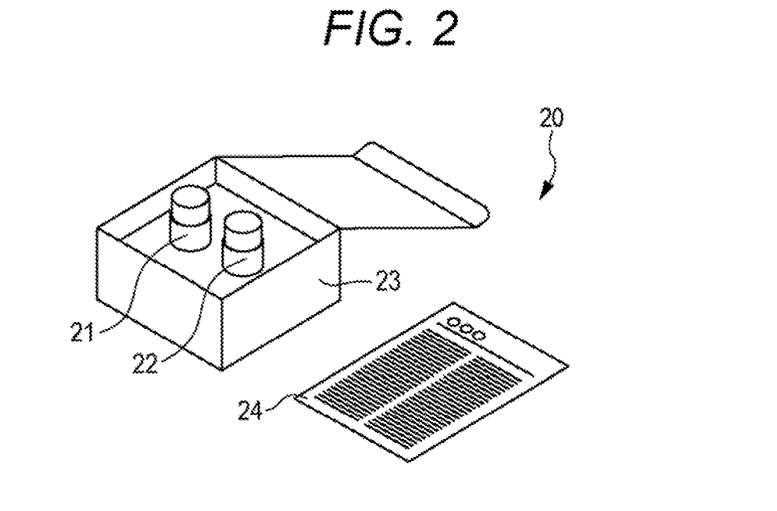
FIG. 2 is a schematic diagram illustrating an example of an APTT reagent kit of the present embodiment.

In the present embodiment, a case accommodating the first reagent and a case accommodating the second reagent may be packed in a box and provided to the user. The package insert describing how to use the APTT reagent kit and the like may be enclosed in the box. FIG. 2 illustrates an example of the APTT reagent kit of the present embodiment. With reference to FIG. 2, 20 indicates the reagent kit of the present embodiment, 21 indicates a first case accommodating the first reagent, 22 indicates a second case accommodating the second reagent, 23 indicates a packing box, and 24 indicates a package insert.

The reagent kit of the present embodiment may further contain a reagent and the like that are usually used in the APTT measurement as other reagents. Examples of such a reagent include plasma for reference and an aqueous medium for dilution. Examples of the plasma for reference include normal plasma, plasma for quality control, plasma deficient in various coagulation factors, LA-containing plasma, and heparin-containing plasma. The aqueous medium for dilution is an aqueous medium for diluting the first reagent. For example, when LA is detected using the reagent kit of the present embodiment equipped with the first reagent containing a phospholipid, the concentration of phospholipid in the first reagent is lowered by diluting the first reagent with an aqueous medium for dilution. By this, the inhibition reaction of phospholipid by LA is more likely to proceed. The APTT measured by the diluted first reagent and the second reagent is called "diluted APTT" (dAPTT) in the field of blood test.

[3. Method for Suppressing Precipitation of Ellagic Acid Compound]

In another embodiment, a method for suppressing the precipitation of an ellagic acid compound is provided. In this method, the precipitation of an ellagic acid compound is suppressed by mixing the ellagic acid compound and a compound represented by Formula (I) in an aqueous solution so that the ellagic acid compound and the compound represented by Formula (I) coexisting in the mixture. The details of the ellagic acid compound and the compound represented by Formula (I) are as described above. The aqueous solution may be an aqueous solvent capable of dissolving the ellagic acid compound and the compound represented by Formula (I). The details of such an aqueous solvent are the same as those described for the aqueous solvent used in the APTT reagent of the present embodiment.

The method for mixing the ellagic acid compound and the compound represented by Formula (I) in an aqueous solution is not particularly limited. For example, the ellagic acid compound may be added to an aqueous solution containing the compound represented by Formula (I). The compound represented by Formula (I) may be added to an aqueous solution containing the ellagic acid compound. Alternatively, an aqueous solution containing the compound represented by Formula (I) and an aqueous solution containing the ellagic acid compound may be mixed together.

As presented in Examples to be described later, when the salt concentration in the aqueous solution which contains the ellagic acid compound but does not contain the compound represented by Formula (I) is increased, the salting-out effect causes the precipitation of the ellagic acid compound. However, when the compound represented by Formula (I) mix with the ellagic acid compound in an aqueous solution, the precipitation of the ellagic acid compound is suppressed even when the salt concentration in the aqueous solution is increased.

[4. Method for Measuring Activated Partial Thromboplastin Time]

The APTT measurement method of the present embodiment (hereinafter, also referred to as "measurement method") includes mixing a blood sample, a first reagent comprising an ellagic acid compound and a compound represented by Formula (I), and a second reagent comprising a calcium ion and measuring the coagulation time. The APTT reagent of the present embodiment described above can be used as the first reagent. Alternatively, the reagent kit of the present embodiment described above can be used as the first reagent and the second reagent.

As the blood sample, blood collected from a subject or plasma prepared from the blood is used. The preferred blood sample is plasma. A known anticoagulant usually used in blood test may be added to the blood sample. Examples of such an anticoagulant include trisodium citrate. When heparin therapy is monitored by the measurement method of the present embodiment, blood or plasma of a subject to which heparin has been administered is used. The blood sample may be incubated before the addition of the first reagent, for example, at a temperature of 35° C. or more and 40° C. or less for a time period of 30 seconds or more and 2 minutes or less.

In the present embodiment, the blood sample and the first reagent are first mixed together. The mixing ratio of the first reagent to the blood sample may be about 8:2 to 2:8 and is preferably 5:5 as a volume ratio. In other words, the amount of the first reagent added may be an amount (volume) to be 0.25 time or more and 4 times or less the amount (volume) of the blood sample. Preferably, the amount of the first reagent added is equal to the amount (volume) of the blood sample. After the blood sample and the first reagent are mixed together, it is preferable to incubate the mixture under a predetermined condition. Examples of the predetermined condition include a condition under which the mixture is incubated at a temperature of 35° C. or more and 40° C. or less for a time period of 2 minutes or more and 5 minutes or less.

Subsequently, the mixture of the blood sample with the first reagent is mixed with the second reagent. Hereinafter, the mixture of the blood sample with the first reagent and the second reagent is also referred to as "measurement sample". The amount of the second reagent added may be an amount (volume) so that the calcium ion concentration in the measurement sample is usually 2 mM or more and 20 mM or less, preferably 4 mM or more and 10 mM or less. The measurement sample may be prepared by a manual method or using a fully automatic measuring instrument Examples of such an instrument include CS series (Sysmex Corporation) of a fully automatic blood coagulation measuring instrument.

In the present embodiment, the coagulation time is measured by taking the time at which the second reagent is added as the measurement start point. The coagulation time may be measured by a manual method or using a fully automatic measuring instrument. In the manual method, the time until fibrin is deposited is measured by visual observation using a stopwatch or the like. When a fully automatic measuring instrument is used, the coagulation time may be measured by an optical measurement method or a physical measurement method. In the optical measurement method, for example, the measurement sample is irradiated with light, the optical information regarding transmittance, absorbance, scattered light intensity, and the like is acquired, and the coagulation time is acquired based on the acquired information. In the physical measurement method, for example, the physical information regarding the viscosity of the measurement sample is acquired using a steel ball and the coagulation time is acquired based on the acquired information. The fully automatic measuring instrument is not particularly limited. For example, CS series (Sysmex Corporation) of a fully automatic blood coagulation measuring instrument can measure the coagulation time based on the optical information such as transmittance, absorbance, and scattered light intensity. STA Compact (Roche Diagnostics Co., Ltd.) of a fully automatic blood coagulation/fibrinolysis measuring instrument can measure the coagulation time based on the physical information such as viscosity.

Hereinafter, the present invention will be described in detail with reference to Examples, but the present invention is not limited to these Examples.

EXAMPLES

Figure 3:
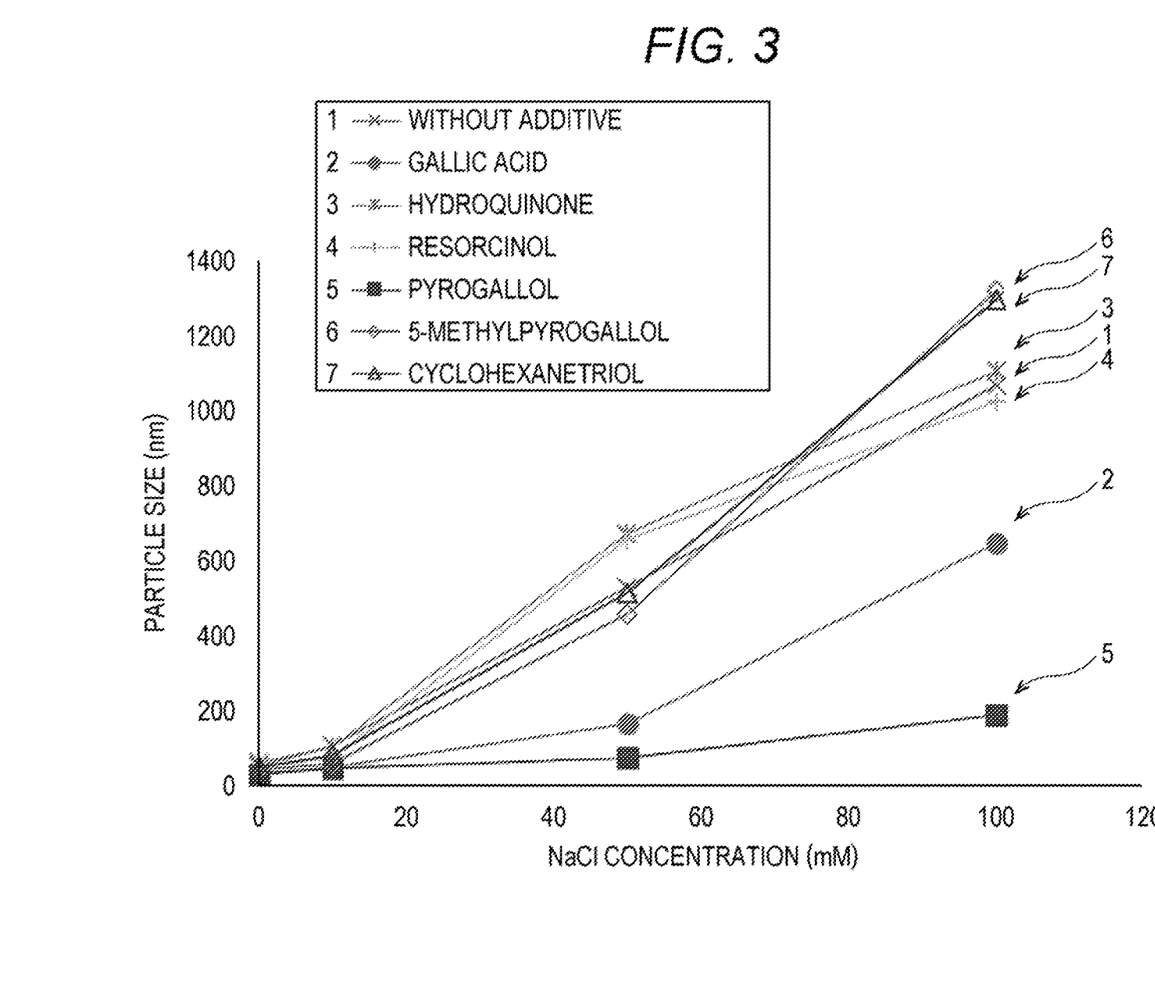
FIG. 3 is a graph illustrating relation between a particle size of a complex and a concentration of sodium chloride in ellagic acid-metal ion complex solutions containing various additives.
Figure 4A:
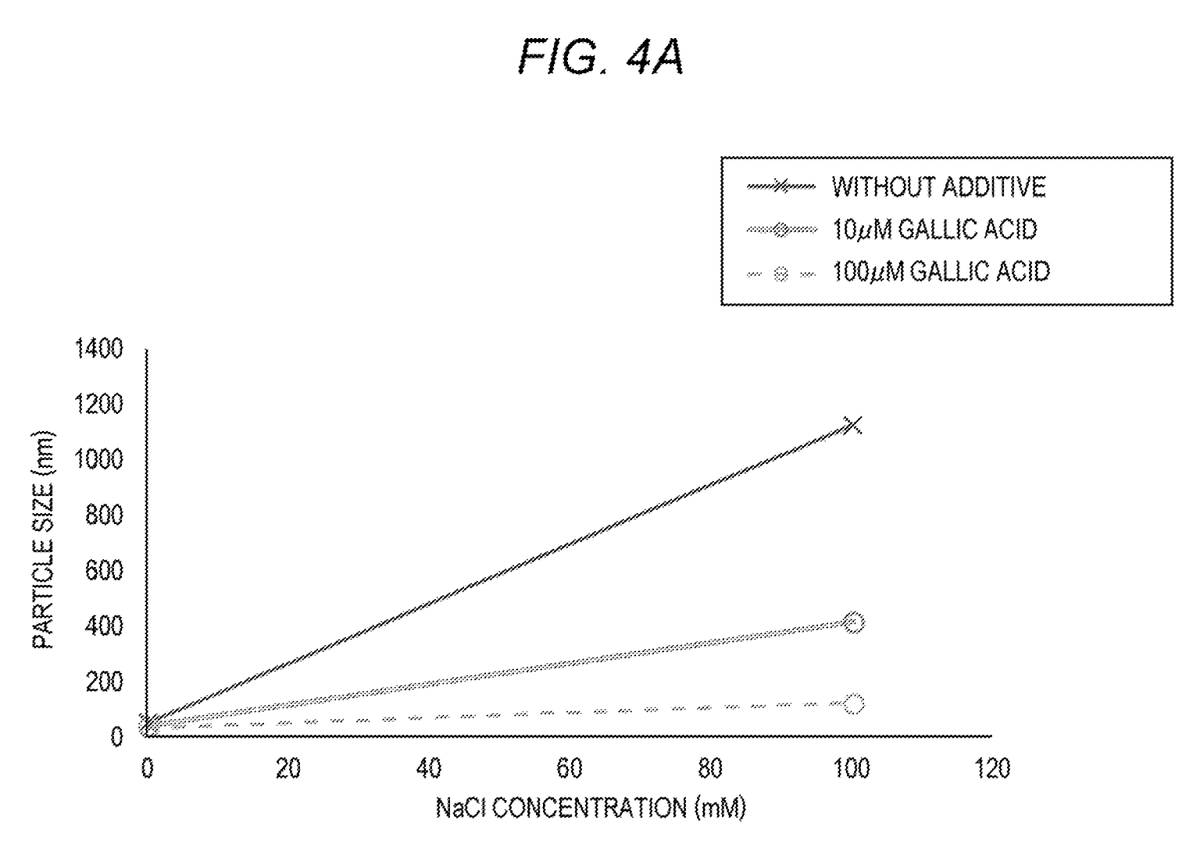
FIG. 4A is a graph illustrating relation between a particle size of a complex and a concentration of sodium chloride in ellagic acid-metal ion complex solutions containing gallic acid at various concentrations.
Figure 4B:
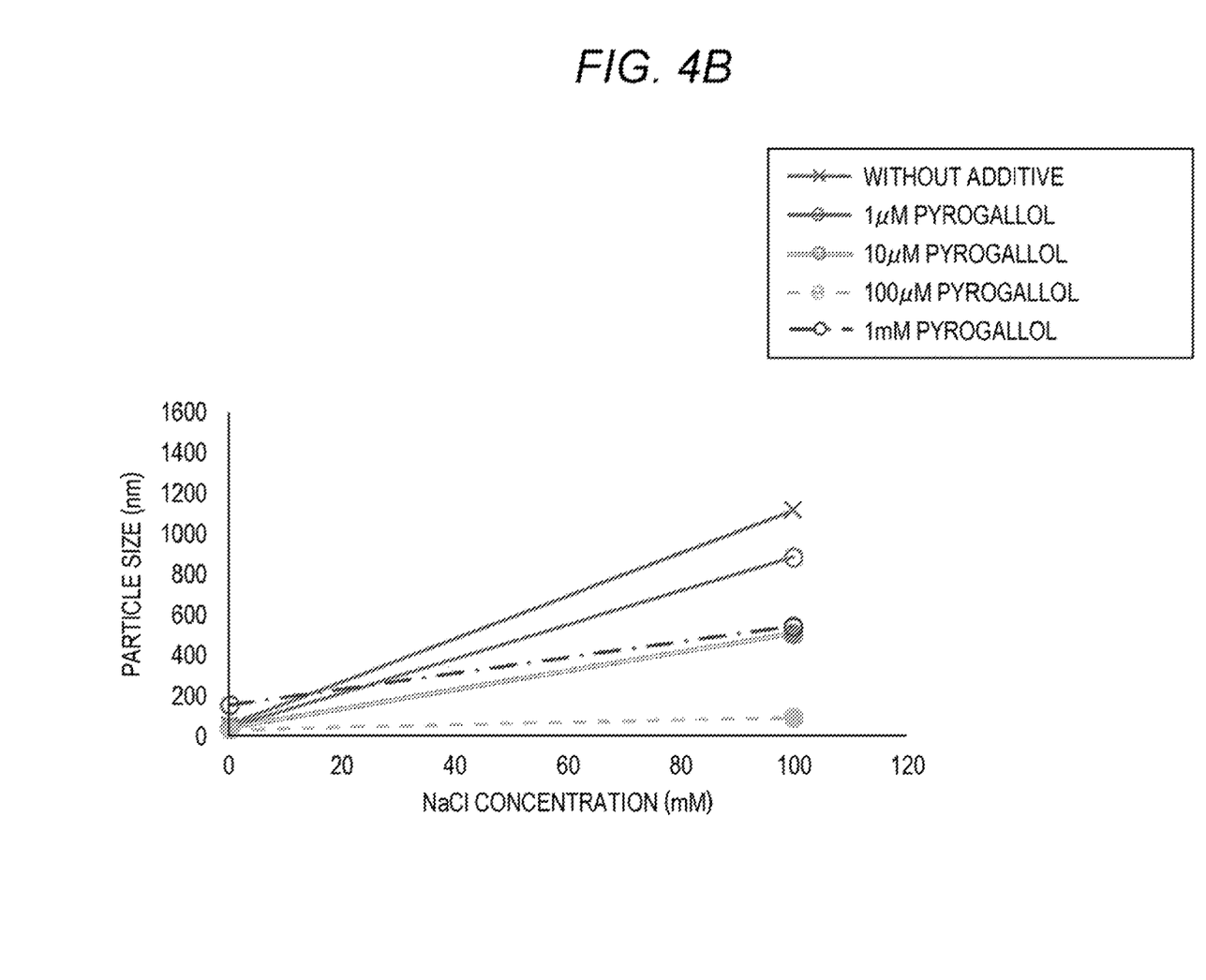
FIG. 4B is a graph illustrating relation between a particle size of a complex and a concentration of sodium chloride in ellagic acid-metal ion complex solutions containing pyrogallol at various concentrations.

Example 1: Investigation on Effect of Suppressing Precipitation of Ellagic Acid Compound In an APTT reagent comprising a metal ion complex of ellagic acid as an activator, when the salt concentration increases, the complex particle size increases by the salting-out effect, and finally precipitation occurs. By utilizing the principle of salting out, the effect of suppressing the precipitation of various additives in ellagic acid-metal ion complex solutions was confirmed.
(1) Preparation of Ellagic Acid-Metal Ion Complex Solution
An ellagic acid-metal ion complex solution was prepared to contain 50 mM HEPES, 8 mM TAPS, and 1% by mass glycine as buffer components, 100 μM ellagic acid, 60 μM zinc chloride, and 50 μM aluminum chloride as a metal ion complex of ellagic acid, and 0.05% ProClin (trademark) 300 (Sigma-Aldrich Co., LLC.) as a preservative. A complex solution comprising each additive at a concentration of 100 μM was obtained by mixing this solution with any one selected from gallic acid, pyrogallol, hydroquinone, 5-methylpyrogallol, resorcinol, or cyclohexanetriol as an additive. As a control, an ellagic acid-metal ion complex solution not comprising an additive was used.
(2) Investigation on Precipitation Suppressing Effect
Each complex solution prepared in (1) above was mixed with a 5 M sodium chloride solution to obtain a mixed solution (test group) having a sodium chloride concentration of 10 mM, 50 mM, or 100 mM. The relationship between the salt concentration in each mixed solution and the average particle size of complex was confirmed by a dynamic scattered light method using Zetasizer Nano (Malvern Panalytical Ltd.). The results are illustrated in FIG. 3. As illustrated in FIG. 3, in the test group to which gallic acid or pyrogallol was added, it has been found that the degree of increase in particle size with respect to the increase in salt concentration is small. In fact, when the sodium chloride concentration is 100 mM, precipitation has not been visually confirmed in the test group to which gallic acid or pyrogallol was added but precipitation has been visually confirmed in the test groups containing additives other than these and the test group not containing an additive.
(3) Investigation on Relationship Between Additive Concentration and Precipitation Suppressing Effect
Gallic acid and pyrogallol, that were observed to have the effect of suppressing the precipitation of complex particles, were added to ellagic acid-metal ion complex solutions at the concentrations illustrated in FIGS. 4A and 4B. The effect of suppressing precipitation was confirmed in the same manner as in (2) above using the complex solutions containing gallic acid or pyrogallol at various concentrations. The results are illustrated in FIGS. 4A and 4B. It has been suggested that the precipitation suppressing effect is observed at all concentrations.

Figure 5:
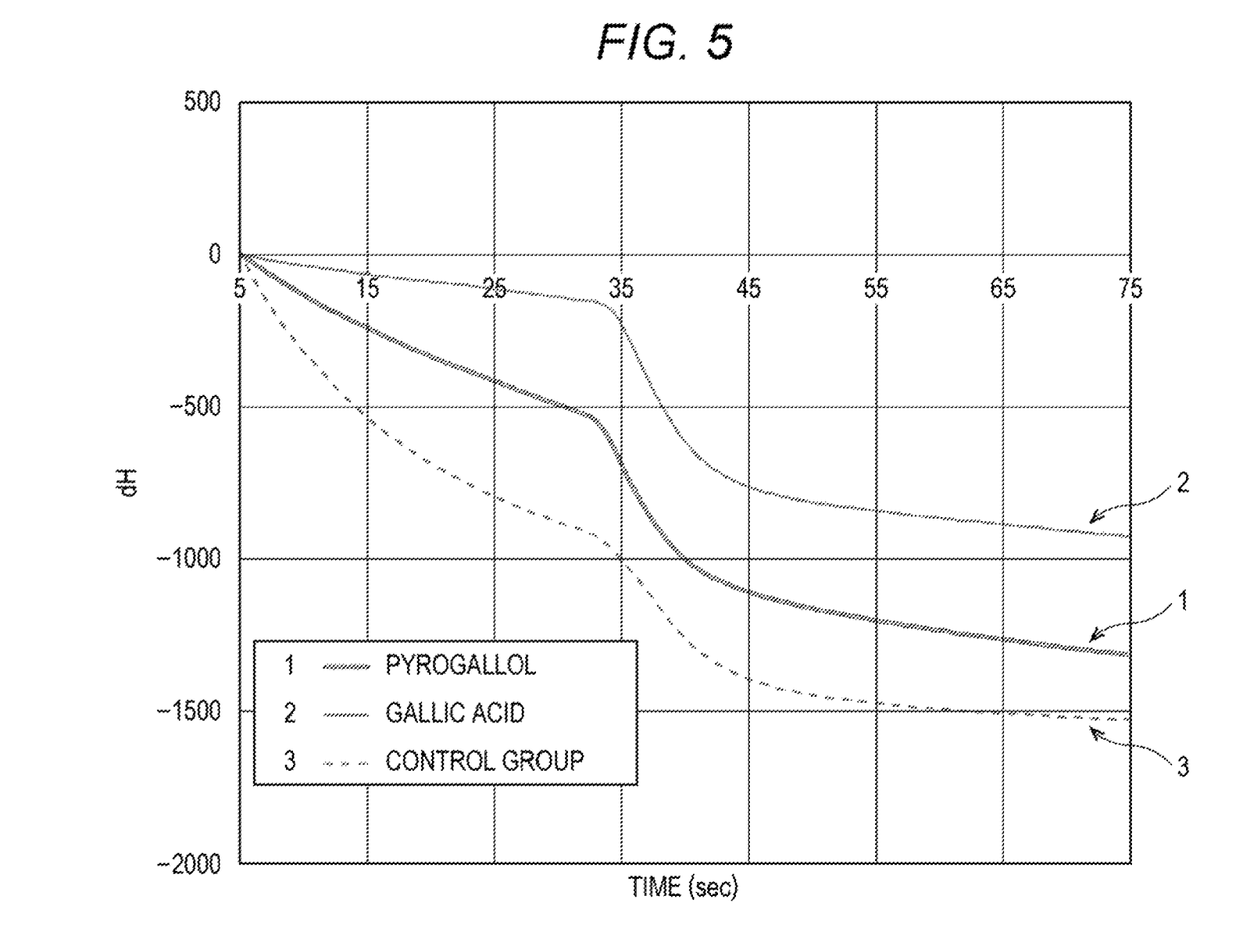
FIG. 5 is a coagulation waveform acquired by optical measurement using an APTT reagent containing gallic acid or pyrogallol.

Example 2: Investigation on Effect of Suppressing Abnormal Initial Reaction for Coagulation It was investigated whether the abnormal initial reaction was suppressed when using an APTT reagent containing pyrogallol or gallic acid.
(1) Preparation of APTT Reagent
An ellagic acid-metal ion complex solution was prepared to contain 50 mM HEPES, 8 mM TAPS, and 1% by mass glycine as buffer components, 100 μM ellagic acid, 60 μM zinc chloride, and 50 μM aluminum chloride as a metal ion complex of ellagic acid, and 0.05% ProClin (trademark) 300 (Sigma-Aldrich Co., LLC.) as a preservative. The complex solution was mixed with gallic acid or pyrogallol as an additive to obtain a complex solution comprising gallic acid or pyrogallol at a concentration of 100 μM. As a control, an ellagic acid-metal ion complex solution not containing an additive was used. PE (L-α-phosphatidylethanolamine), PC (L-α-phosphatidylcholine), and PS (L-α-phosphatidylserine) as a phospholipid component were added to the respective complex solutions so as to have final concentrations of 10 mg/dL, 45 mg/dL, and 5 mg/dL, respectively, thereby preparing APTT reagents. The concentration of gallic acid and pyrogallol in the respective APTT reagents were 0.013% by mass and 0.009% by mass, respectively. In the respective APTT reagents, the concentration of gallic acid and pyrogallol per 100 parts by mass of ellagic acid were 43 parts by mass and 32 parts by mass, respectively.
(2) Investigation on Effect of Suppressing Abnormal Initial Reaction
Pseudo samples were prepared to induce an abnormal initial reaction for coagulation by adding very low density lipoprotein (VLDL) and C-reactive protein (CRP) to frozen plasma so as to have final concentrations of 100 μg/mL and 300 μg/mL, respectively. These pseudo samples were subjected to the APTT measurement using a fully automatic coagulation measuring instrument CS-5100 (Sysmex Corporation) set with the reagent prepared in (1) above and a calcium ion-containing reagent, and the coagulation waveforms thereof were acquired. FIG. 5 illustrates the coagulation waveforms acquired by the measurement using the respective APTT reagents.

As illustrated in FIG. 5, in the control group (APTT reagent not containing an additive), the optical measurement value has sharply decreased immediately after the addition of the reagent and abnormal initial reaction for coagulation has been observed. On the other hand, in the test group using the APTT reagent comprising gallic acid or pyrogallol, it has been confirmed that the decrease in the optical measurement value after the addition of the reagent is gradual and the abnormal initial reaction for coagulation has decreased.

What is claimed is:
1. A method for measuring activated partial thromboplastin time, the method comprising:
mixing: a blood sample; a first reagent comprising ellagic acid and pyrogallol; and a second reagent comprising a calcium ion; and measuring activated partial thromboplastin time using the mixture prepared in the mixing step.

2. The method according to claim 1, wherein the mass % of the pyrogallol in the first reagent is from 0.001% to 0.02%.

3. The method according to claim 1, wherein the mass of the pyrogallol is from 5 to 65 parts per 100 parts of the ellagic acid.

4. The method according to claim 1, wherein the first reagent further comprises at least one metal ion.

5. The method according to claim 3, wherein the at least one metal ion is selected from the group consisting of a zinc ion, an aluminum ion, and a manganese ion.

6. The method according to claim 1, wherein the first reagent further comprises a nonpolar amino acid.

7. The method according to claim 6, wherein the at least one nonpolar amino acid is at least one selected from the group consisting of glycine, alanine, and phenylalanine.

8. The method according to claim 6, wherein the concentration of the nonpolar amino acid in the first reagent is 0.75% by mass or more.

9. The method according to claim 6, wherein the concentration of the nonpolar amino acid in the mixture prepared in the mixing step is 0.25% by mass or more.

10. The method according to claim 1, wherein the first reagent further comprises a phospholipid.

11. The method according to claim 10, wherein at least one phospholipid is at least one selected from the group consisting of phosphatidylserine, phosphatidylethanolamine, and phosphatidylcholine.

12. A method for measuring activated partial thromboplastin time, the method comprising:
- a first mixing step of mixing a blood sample and a first reagent comprising i) ellagic acid, ii) at least one metal ion, and iii) pyrogallol;
- a second mixing step of mixing a second reagent comprising a calcium ion and a mixture prepared in the first mixing step; and
- a measuring step of measuring activated partial thromboplastin time using the mixture prepared in the second mixing step,
- wherein the at least one metal ion is selected from the group consisting of a zinc ion, an aluminum ion, and a manganese ion.

13. The method according to claim 12, wherein the first reagent further comprises at least one nonpolar amino acid selected from the group consisting of glycine, alanine, and phenylalanine.

* * * * *